United States Patent
Pfirrmann

Patent Number: 6,011,030
Date of Patent: Jan. 4, 2000

[54] METHOD OF TREATING SYMPTOMS OF MICROBIAL INFECTION OR SEPSIS

[75] Inventor: Rolf W. Pfirrmann, Lucerne, Switzerland

[73] Assignee: Ed. Geistlich Söhne AG für Chemische Industrie, Switzerland

[21] Appl. No.: 08/934,753

[22] Filed: Sep. 22, 1997

[51] Int. Cl.[7] .................................................. A61K 31/54
[52] U.S. Cl. ........................................................ 514/222.2
[58] Field of Search .......................................... 514/222.2

[56] References Cited

U.S. PATENT DOCUMENTS

| | | |
|---|---|---|
| 3,423,408 | 1/1969 | Pfirrmann . |
| 4,096,241 | 6/1978 | Geistlich et al. . |
| 4,107,305 | 8/1978 | Pfirrmann . |
| 4,337,251 | 6/1982 | Pfirrmann . |
| 4,587,268 | 5/1986 | Pfirrmann . |
| 4,604,391 | 8/1986 | Pfirrmann . |
| 4,626,536 | 12/1986 | Pfirrmann . |
| 4,772,468 | 9/1988 | Pfirrmann . |
| 4,960,415 | 10/1990 | Reinmüller . |
| 5,077,281 | 12/1991 | Reinmüller . |
| 5,210,083 | 5/1993 | Pfirrmann . |
| 5,593,665 | 1/1997 | Pfirrmann et al. . |

*Primary Examiner*—Laurie Scheiner
*Attorney, Agent, or Firm*—Rothwell, Figg, Ernst & Kurz, p.c.

[57] ABSTRACT

In accordance with the present invention, a method of treating a patient with symptoms of microbial infection and/or sepsis involves first administering to the patient an antimicrobial amount of a cell wall constituent-inactivating, endotoxin non-releasing, and/or exotoxin-inactivating antimicrobial compound such as Taurolidine and/or Taurultam, without administration of an antibiotic to the patient and prior to administration of such antibiotic. The Taurolidine and/or Taurultam are administered locally or intravenously to the patient to substantially inactivate microbes that are causing the infection. Only after substantially inactivating the microbes causing the infection with the Taurolidine and/or Taurultam, is an antibiotic administered to the patient.

12 Claims, No Drawings

METHOD OF TREATING SYMPTOMS OF MICROBIAL INFECTION OR SEPSIS

BACKGROUND OF THE INVENTION

1. Field of the Invention

The present invention relates to the field of treating patients having symptoms of microbial infections or sepsis, with the aim to reduce the high mortality and morbidity that results from the septic process.

2. Description of the Background Art

The treatment of severe microbial infection, bacteraemia and sepsis, accompanied by the presence of massive gram-negative and gram-positive bacterials or fungi, i.e. candida spp, including pus, is quite complex and difficult to treat by conventional methods. Those infections include, but are not restricted to, surgical infections, severe abdominal infections such as peritonitis, pancreatitis, gall bladder empyema, pleura empyema, as well as bone infections such as osteomyelitis. In hospitals several situations have been associated with the development of septicaemia, sepsis and septic shock, including use of immuno-suppressants (corticosteroids), chemotherapy, radiation, contaminated i.v. fluids, haemorrhagic shock, ischaemia, trauma, cancer, immuno-deficiency, virus infections, diabetes, various forms of infections from Internal Medicine, and sepsis following nosocomial gram-negative and gram-positive infections.

Many patients develop severe infections while treated with antibiotic therapy. Because conventional powerful broad-spectrum antibiotics rapidly rupture microbial cell walls, administration of antibiotics to critically ill patients with severe microbial infection can endanger the life of the patient. This can occur by massive release of bacterial endo-toxins, which include lipopolysaccharide (LPS) components of the outer membrane of gram-negative bacteria, and are pivotal in triggering sepsis and shock. This is precipitated by the antibiotic attack on the bacterial outer membrane, or disturbing the murein synthesis, protein biosynthesis, or DNA-topology (gyrase-inhibitors)of the organism.

Sepsis also often results from a gram-positive bacterial infection, especially of streptococcus or staphylococcus species, and their exo-toxins. Also, the protein component of the bacterial endotoxins from the bacterial outer membrane (OM) play an important role in the pathogenesis of sepsis. Bacterial translocation, by disruption of the gut barrier, functions by the passage of viable bacteria through the epithelial mucosa and lamina propria of the gastrointestinal tract to the lymph nodes, spleen, liver, peritoneum and blood, thus becoming a further source of endotoxins.

The broad use of antibiotics also significantly influences multiresistance of microorganisms and results in bacterial overgrowth.

The release of toxins, triggered by the action of antibiotics on microbial cells, in the first instance activates the patient's defense mechanisms, i.e. the blood monocytes, leucocytes and macrophages of the patient, mediated by endogenous glycoproteins known as cytokines, in order to protect the patient's body from infection. In patients with symptoms of severe infection, the toxic effects are as follows. The above-noted cytokines progress in overreaction of the host, in a type of cascade, through the release of further cytokines such as TNF-α (Tumor Necrosis Factor), one of the primary mediators of the septic process, and Interleukins (IL-1α, IL-β, IL-6 etc.), resulting in tissue damage from such an excessive release of mediators. Thus, administration of antibiotics leads first to a rise in TNF-a and secondly other cytokines and factors like leukotrienes prostaglandins, thromboxane, PAF (platelet activating factors), and gamma-interferon. If the liberation of toxins (including endotoxins and endotoxins) continues due to the activity of antibiotics on the microbes, an enormous rise in cytokines results in an over-reaction of the patient's defense systems, culminating in sepsis, sepsis syndrome and septic shock (Mediator disease), and subsequent death of the patient by multiorgan failure.

In animal experiments on peritonitis models, with massive bacterial introduction in the abdominal cavity, using mice, rats and rabbits injected, i.e., with pure bacterial cultures of E. coli and Bacteroides fragilis, nearly 100% of infected animals die when using intraperitoneally (i.p.) delivered conventional bactericidal antibiotics and quick-working antiseptics such as povidone-iodine. For example, povidone-iodine leads to a massive release of bacterial toxins. The bacteraemia disappears for a short period of time, but ultimately a massive reinfection takes place whereby the host body's immunity is almost completely destroyed by the release of bacterial toxin, with substantially 100% lethality.

Even in cases where the life of a sepsis patient is initially saved using antibiotics, there exists only a small long-term chance of survival following the occurrence (approximately 3 years), because of the damage caused to the patient's organs (organ failure) by the bacterial toxins.

The compounds Taurolidine (Taurolin ®) and Taurultam are known antimicrobial substances with broad-spectrum activity against aerobic and anaerobic bacteria, mycobacteria and fungi. Unlike antibiotics, these compounds do not result in release of large quantities of bacterial toxins. They have been suggested as a substitute for antibiotics for administration in patients both to combat infections and to deal with sepsis and septic shock.

There remains an urgent need in the art for improved methods of treating patients with severe microbial infections.

SUMMARY OF THE INVENTION

In accordance with the present invention, a method of treating a patient with severe microbial infection comprises first administering to the patient an antimicrobial amount of a cell wall constituent-inactivating, endotoxin non-releasing, and/or exotoxin-inactivating antimicrobial compound, without and prior to administration of an antibiotic to the patient. The antimicrobial compound is administered to the patient to substantially inactivate gram-negative and gram-positive microbes and their toxins that are causing the infection. Only after substantially inactivating the masses of microbes causing the infection with the antimicrobial compound, e.g., by removed focus or surgical intervention and Taurolin treatment, is an antibiotic administered to the patient.

DETAILED DESCRIPTION OF THE PREFERRED EMBODIMENTS

As used herein, the term "patient" refers to a mammalian patient, preferably a human patient with microbial infection.

The antimicrobial compounds utilized in accordance with the invention are cell wall constituent-inactivating, endotoxin non-releasing, and/or exotoxin inactivating antimicrobial compounds, which are slow-acting bactericides. Preferably, the compounds are cell wall-crosslinking compounds such as Taurolidine and Taurultam.

The compounds Taurolidine and Taurultam are as disclosed in U.S. Pat. No. 5,210,083, incorporated herein by reference.

The term "antibiotic" as used herein refers to conventional antibiotics as ordinarily understood in the art, i.e., antibiotics that act by attacking, breaking and/or rupturing microbial cell walls (disturbance of murein-biosynthesis, protein-biosynthesis, DNA topology, etc.), resulting in release of microbial toxins from the microbial cells.

While the invention is further described with respect to Taurolidine and Taurultam, the invention also is applicable to use of other cell wall constituent-inactivating, antimicrobial compounds which release no or substantially insignificant bacterial toxins.

As indicated above, the present invention is directed to a method of treating a patient with microbial infection, such as bacterial and/or fungal infection, especially nosocomial infections as, for instance, caused by E. coli, klebsiella sp., enterobacter sp., proteus sp., serratia marcescens, pseudomonas aeruginosa, staph. aureus, coag.-negative staphylococcus, enterococcus sp., streptococcus pneumoniae, haemophilus influenzae, bacteroides sp., acinetobacter sp., candida sp., etc., and is particularly advantageous for the treatment of severe microbial infection, e.g. nosocomial infections with resistant germs methicillin-resistant Staphylococcus aureus (MRSA) and vancomycin-resistant Enterococcus faecalis (VRE). After identifying a patient exhibiting symptoms of microbial infection, toxic effects of microbial infection or sepsis, antimicrobial amounts of Taurolidine and/or Taurultam are administered intraperitoneally or intravenously to the patient, without and prior to administration of an antibiotic, so as to substantially inactivate microbes and their toxins that are causing the infection. Thereafter, for instance postoperatively, an antibiotic can be administered.

In preferred embodiments, after administration of the Taurolidine and/or Taurultam, and prior to administration of the antibiotic to the patient, the source of the infection (focus) is, for instance, surgically removed from the patient, and/or toxic amounts of purulent material resulting from the infection are removed from the patient.

At the time of administration of the antibiotic to the patient, Taurolidine and/or Taurultam can optionally be co-administered to the patient with the antibiotic.

In preferred embodiments, the Taurolidine and/or Taurultam is initially administered substantially continuously for a time period of about 3–5 days prior to administration of an antibiotic to the patient.

In particularly preferred embodiments, the Taurolidine and/or Taurultam is administered in an aqueous solution at a concentration of about 0.1–3% (e.g., 0.5%) by weight Taurolidine and/or Taurultam. Suitable compositions are disclosed in the previously mentioned U.S. Pat. No. 5,210,083. In most preferred embodiments, the aqueous solution of Taurolidine and/or Taurultam is administered during the previously mentioned 3–5 day time period in a total amount of about 0.5–5 liters (preferably corresponding to 1 liter/2% per day, 20–30 gms/24 hours/adult human patient of Taurolidine). The solution of Taurolidine and/or Taurultam can be administered to the patient intraperitoneally as lavage, or instillation prior to closure, or intravenously via central catheter by drop infusion s, and/or locally at the internal site of the infection by catheter introduction, e.g., in to the boay cavities or the infected wound area.

In certain embodiments in which a large amount of purulent material is not present in the infected patient, surgical removal of the source of infection and/or purulent material may not be necessary. In preferred aspects according to this embodiment, Taurolidine and/or Taurultam is administered for approximately 3–5 days without antibiotic administration, after which antibiotics or combinations of antibiotics can be administered to the patient with or without further Taurolidine and/or Taurultam administration.

Treatment of severe microbial infection in accordance with the present invention can save the lives of many patients, as compared to conventional treatments. Taurolidine and Taurultam destroy bacteria slowly, cross-linking the bacterial cell walls and thereby preventing the release of bacterial toxins. The cross-linking of the bacterial cell walls inactivates the bacterial toxins which could otherwise be highly poisonous. Additionally, because of this unique mode of action with bacterial cell walls, no resistance development by microbe has been observed.

Taurolidine and/or Taurultam prevent over-production of cytokines by the patient. While addition of antibiotics to human blood leads to a rise in TNF-a, the addition of Taurolidine and/or Taurultam to antibiotic-treated cultures prevents a rise in TNF production as a result of nearly complete neutralization of released endotoxins.

While antibiotics act quickly, Taurolidine and/or Taurultam kills bacteria slowly. Furthermore the bacteraemia disappears slowly while the efficacy of Taurolidine and/or Taurultam continues over a longer period of time. Bacterial toxins are prevented from release, and no sepsis cascade is precipitated by over-production of cytokines.

Accordingly, in cases of severe bacterial or other microbial infection, Taurolidine and/or Taurultam should be introduced to the patient first in accordance with the present invention, without administration of antibiotics. The toxic source of the infection focus) and/or toxic amounts of purulent material resulting from the infection then can be removed, and antibiotics are thereafter introduced as a prophylactic measure with or without co-administration of and/or Taurultam.

The invention is illustrated by the following Examples, which are not intended to be limiting.

EXAMPLE 1

Severe Peritonitis

In a typical abdominal procedure by laparotomy or laparoscopic procedure which should not be considered as limited, 1 liter of 0.5% Tauroline Ringer Solution (0.5% Taurolidine), is, after abdominal toilette (cleansing) with 2–3 liters of saline, rinsed at body temperature through a suction rinse tube under slight pressure, left in situ for 10 minutes and thereafter again removed by aspiration.

Depending on the extent of surgical invasion and peritoneal infection 200–250 ml of Taurolin Solution 2% (2% Taurolidine) is instilled at 37° C. and allowed to remain in the abdominal cavity after conclusion of the operative procedure.

Intraoperatively drop-infusions via central catheter of 250 ml Taurolin 2% Solution (2% Taurolidine) are to be administered in 4 to 6 hourly intervals during the first operation day and every 6 hours for the next 3 to 4 days without concomitant antibiotic therapy (dosage for adults: 20–30gms Taurolidine /24 h).

After the 3rd or 4th day antibiotics may be given in accordance to the sensitivity test against the respective bacteria (antibiogram).

EXAMPLE 2

Appendicitis perforata

After laparotomy, aspiration of pus and removal of appendix is accomplished according to known surgical principles.

Thereafter repeated local rinsing of the operating field (not the entire abdomen) with 200–300 ml of 0.5% Tauroline Ringer Solution (0.5% Taurolidine) at 37° C., after 10 minutes contact time aspiration of the rinsing solution. Thereafter drainage of the Douglas-room: after closure of the peritoneum, 100–200 ml of Taurolin Solution 2% (2% Taurolidine) are filled into the drain which is then closed.

Postoperatively an antibiotic of choice is administered in accordance with the antibiogram.

EXAMPLE 3

Staphylococcus septicaemia

Case report

This Example demonstrates the danger of administering antibiotics prior to Taurolidine treatment according to the present invention.

Course of disease

Severe infection of the psoas muscle of a 14 year old boy with pain in the right iliac fossa and right thigh, accompanied by general malaise, with vomiting, dysuria and dark coloured urine.

After intravenous doses of Cefotaxime and Flagyl, thin watery pus was obtained by aspiration which contained gram-positive cocci, and Netilmycin was given instead of Cefotaxime. The boy was extremely toxic, had generalized myalgia, a stiff neck and pain in the right iliac fossa. The culture finally gave a growth of Staph. aureus resistant to Penicillin, Ampicillin and Amoxyllin. Intravenous Fucidin was added, but the boy's condition was getting worse. On the advice of the Infectious Diseases Physicians Chloramphenicol was added to the antibiotic mixture. The temperature was rising to 40° C., The boy's condition was extremely critical and the antibiotics were all stopped.

Taurolin® treatment

An initial dose of 4 gms was given intravenously as Taurolin® 2% Solution via central catheter over four hours, and thereafter 2 gms were given every six hours being infused by drop infusion over a two hour period. On starting the Taurolin® the temperature immediately fell to 37° C. and by the following day the boy had very much improved. Every time the Taurolin® infusion was started the temperature came down and the toxicity disappeared.

Antibiotics treatment

Following the Taurolin® treatment for 4 days antibiotics such as Cefotaxime, Flucloxacillin and Flagyl were recommended but they were only maintained for two or three days. After recovery one month after admission the boy was finally able to go home.

I claim:

1. A method of treating a patient with bacterial infection, so as to prevent release of bacterial endo-toxins, comprising:

a) identifying a patient exhibiting symptoms of infection by bacteria, said bacteria having bacterial endotoxins;

b) administering to said patient an antimicrobial amount of an antimicrobial compound which is selected from the group consisting of non-antibiotic antimicrobial compounds which are cell wall constituent-inactivating by cell wall crosslinking, non-antibiotic antimicrobial compounds which are endotoxin non-releasing, non-antibiotic antimicrobial compounds which are exotoxin-inactivating, and combinations thereof, without administration of an antibiotic to said patient and prior to substantial administration of any antibiotic to said patient subsequent to step a) above, so as to substantially inactivate said bacteria without releasing said endo-toxins and substantially reduce said symptoms; and c) then, after substantially inactivating in step b) said bacteria without releasing said endo-toxins and substantially reducing said symptoms with said antimicrobial compound, administering an antibiotic to said patient.

2. The method of claim 1 wherein step a) comprises identifying in said patient symptoms of severe sepsis resulting from infection by gram-negative bacteria, and wherein in step b) said gram-negative bacteria is substantially inactivated without releasing said endo-toxins, and further wherein said antimicrobial compound is a bacterial cell wall-crosslinking compound with bacterial antitoxin activity.

3. The method of claim 1 wherein said antimicrobial compound is selected from a group consisting of Taurolidine, Taurultam and a mixture thereof.

4. The method of claim I wherein during step c), said antimicrobial compound is co-administered with said antibiotic.

5. The method of claim 1 wherein between step b) and c), a source of said infection is surgically removed from said patient.

6. The method of claim 1 wherein between step b) and c), toxic amounts of purulent material resulting from said infection are removed from said patient.

7. The method of claim 3 wherein said antimicrobial compound is administered substantially continuously for a time period of about 3–5 days prior to the administration of said antibiotic.

8. The method of claim 7 wherein said antimicrobial compound is administered in an aqueous solution at a concentration of about 0.1–3% by weight.

9. The method of claim 8 wherein said aqueous solution of said antimicrobial compound is administered during said time period in a total amount of about 0.5–5 liters.

10. The method of claim 8 wherein said aqueous solution is administered so as to provide said patient with an amount of said antimicrobial compound corresponding to about 20–30 grams/24 hours/adult human patient of Taurolidine.

11. The method of claim 9 wherein said antimicrobial compound is administered intravenously.

12. The method of claim 9 wherein said antimicrobial compound is administered locally at a site of said infection, by catheter introduction.

* * * * *